United States Patent
Chan et al.

(10) Patent No.: US 10,910,112 B2
(45) Date of Patent: Feb. 2, 2021

(54) APPARATUS FOR PATIENT RECORD IDENTIFICATION

(71) Applicant: KONINKLIJKE PHILIPS N.V., Eindhoven (NL)

(72) Inventors: Tak Ming Chan, Shanghai (CN); Choo Chiap Chiau, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 85 days.

(21) Appl. No.: 16/186,688

(22) Filed: Nov. 12, 2018

(65) Prior Publication Data
US 2019/0172592 A1    Jun. 6, 2019

(30) Foreign Application Priority Data
Dec. 26, 2017 (EP) ..................... 17210578

(51) Int. Cl.
    *G16H 50/70*    (2018.01)
    *G16H 10/60*    (2018.01)
    *G06F 16/245*   (2019.01)

(52) U.S. Cl.
    CPC ........... *G16H 50/70* (2018.01); *G06F 16/245* (2019.01); *G16H 10/60* (2018.01); *G06F 2216/03* (2013.01)

(58) Field of Classification Search
    CPC .............................................. G06Q 50/22–24
    See application file for complete search history.

(56) References Cited

U.S. PATENT DOCUMENTS

| | | |
|---|---|---|
| 6,604,115 B1 | 8/2003 | Gary et al. |
| 9,305,039 B2 | 4/2016 | Wang et al. |

(Continued)

FOREIGN PATENT DOCUMENTS

| | | |
|---|---|---|
| WO | 2017044802 A1 | 3/2017 |
| WO | 2017158472 A1 | 9/2017 |

OTHER PUBLICATIONS http://www.sas.com/en_in/home.html.
http://www-01.ibm.com/software/analytics/spss/.

*Primary Examiner* — Neal Sereboff (57) ABSTRACT

In a patient record identification apparatus, at least one query value relating to at least one medical condition is input (210). Patient records are received (220) from a patient database. Each patient record includes at least one attribute value relating to the at least one medical condition, and each patient record includes information relating to an outcome of the at least one medical condition. A first set of patient records is determined (230) based on a similarity between the at least one query value input by the user and the at least one attribute value for the patient records. The first set of patient records is separated (240) into patient records relating to a positive outcome and into patient records relating to a negative outcome. An implemented model calculates (250) at least one outcome probability for the at least one medical condition for each patient record of the first set of patient records based on the at least one attribute value for each patient record of the first set of patient records. A second set of patient records is determined (260) from the first set of patient records including a number of patient records in a first sub-set of the patient records relating to the positive outcome and a number of patient records in a second sub-set of the patient records relating to the negative outcome and the at least one outcome probability for the at least one medical condition for each patient record of the first sub-set and second sub-set of the patient records.

9 Claims, 2 Drawing Sheets

(56) References Cited

U.S. PATENT DOCUMENTS

| | | |
|---|---|---|
| 9,361,355 B2 | 6/2016 | Anderson et al. |
| 2010/0312798 A1 | 12/2010 | Dutta et al. |
| 2012/0041772 A1* | 2/2012 | Ebadollahi ............. G16H 10/60 |
| | | 705/2 |
| 2012/0290278 A1* | 11/2012 | Loohius ................. G16H 50/50 |
| | | 703/11 |
| 2013/0226616 A1 | 8/2013 | Nigam et al. |
| 2014/0089003 A1 | 3/2014 | Frey et al. |
| 2014/0172870 A1 | 6/2014 | Wang et al. |
| 2014/0379356 A1* | 12/2014 | Sachdeva ............... A61C 7/002 |
| | | 705/2 |
| 2015/0161346 A1 | 6/2015 | Hu et al. |
| 2015/0227710 A1* | 8/2015 | Pappada ................. G06Q 50/22 |
| | | 705/2 |
| 2016/0004840 A1 | 1/2016 | Rust et al. |
| 2017/0053064 A1 | 2/2017 | Bhavani |
| 2019/0000350 A1* | 1/2019 | Narayan ............. A61B 5/0823 |

\* cited by examiner

APPARATUS FOR PATIENT RECORD IDENTIFICATION

CROSS-REFERENCE TO RELATED APPLICATIONS

This patent application claims the benefit of European Patent Application Number 17210578.5, filed on Dec. 26, 2017 and International Application No. PCT/CN2017/114392, filed on Dec. 4, 2017, the contents of which are herein incorporated by reference.

FIELD OF THE INVENTION

The present invention relates to an apparatus for patient record identification, to a system for patient record identification, to a method for patient record identification, as well as to a computer program element.

BACKGROUND OF THE INVENTION

The general background of this invention is the field of identifying patient records. Cardiovascular Information Systems (CVIS) have been available for many years in the healthcare industry. One activity of utilizing information and preferably knowledge from CVIS or Clinical Data repositories (CDR) is to find historical cases that match certain new patient or query criteria so as to provide valuable reference to the decision maker, e.g. the care giver or the physician. However, finding an exactly matched case (record) from the past is almost impossible, and retrieving cases (records) with loosely matching criteria can result in very large number of cases being identified, without clear clues of the patient's risk of adverse events such as major cardiovascular adverse events (MACE). It is desirable to retrieve historical cases that both have similar observed properties to the query and share close risk (or probability) of adverse events relating to a medical condition, such as cardiovascular disease (CVD).

US2014/0172870A1 describes systems and methods for indexing data include formulating an objective function to index a dataset, a portion of the dataset including supervision information. A data property component of the objective function is determined, which utilizes a property of the dataset to group data of the dataset. A supervised component of the objective function is determined, which utilizes the supervision information to group data of the dataset. The objective function is optimized using a processor based upon the data property component and the supervised component to partition anode into a plurality of child nodes.

SUMMARY OF THE INVENTION

It would be advantageous to have an improved apparatus and associated method for patient record identification, and an improved system for patient record identification, enabling the most relevant patient records for particular purposes to be retrieved.

It should be noted that the following described aspects and examples of the invention apply also for the apparatus for patient record identification, the system for patient record identification, the method for patient record identification, and for the non-transitory computer-readable medium.

According to a first aspect, there is provided an apparatus for patient record identification, comprising:

an input unit; and
a processing unit.

The input unit is configured to enable a user to input at least one query value relating to at least one medical condition. The input unit is configured also to receive patient records from a patient database, wherein each patient record comprises at least one attribute value relating to the at least one medical condition. The processing unit is configured to determine a first set of patient records based on a similarity between the at least one query value input by the user and the at least one attribute value for the patient records. The processing unit is configured also to separate the first set of patient records into patient records relating to a positive outcome for the at least one medical condition and into patient records relating to a negative outcome for the at least one medical condition. The processing unit is configured also to implement a model to calculate at least one outcome probability for the at least one medical condition for each patient record of the first set of patient records based on the at least one attribute value for each patient record of the first set of patient records. The processing unit is configured also to determine a second set of patient records from the first set of patient records. The determination comprises at least one comparison comprising utilization of a number of patient records in a first sub-set of the patient records relating to the positive outcome and comprising utilization of a number of patient records in a second subset of the patient records relating to the negative outcome and comprising utilization of the at least one outcome probability for the at least one medical condition for each patient record of the first sub-set and second sub-set of the patient records.

In other words, a predefined similarity input by a user is used to determine a loosely matched first set of patient records, and target patient records are determined from this set on the basis of predicted values for the output of a medical condition calculated on the basis of attribute values for the patient records compared with information relating to the actual outcomes of the medical condition. To put this another way, patient records are retrieved, and are stratified through categorization on at least one medical condition outcome probability, on the actual outcomes, and further on the grouping of the matched properties. In this manner, the most appropriate patient records can be determined that relates back to the original predetermined similarity input by the user. To put this another way, information and knowledge in a clinical data repository (CDR) also called a patient database, is used to find historical cases that match certain new patient or query criteria in order to provide valuable reference to the decision maker, such as a care giver or physician. This is achieved by identifying historical cases for retrieval that have both similar observed properties to the query and share a close risk (or probability) of adverse events, such as a negative outcome of at least one medical condition.

In an example, the at least one comparison comprises a first comparison between a first ratio of the number of patient records in the first sub-set of the patient records to the number of patient records in the second set of patient records with an average value of the at least one outcome probability for the at least one medical condition for each patient record of the first sub-set of patient records. The at least one comparison also comprises a second comparison between a second ratio of the number of patient records in the second sub-set of the patient records to the number of patient records in the second set of patient records with an average value of the at least one outcome probability for the at least one medical condition for the patient records of the second sub-set of patient records.

In other words, predicted probabilities for medical conditions can be compared to actual probabilities generated from the historical records, enabling the target patient records to be better determined. Thus, a predefined similarity threshold is applied on a query and a set of loosely matched past cases can be retrieved. Then on this candidate set there are labels of the actual outcome, and the candidate set is separated cases with a positive outcome and cases with a negative outcome. The matching mechanism, considering both similarity and outcome probability, shortlists subsets of both the positive outcome cases and the negative outcome cases such that predicted outcome probabilities of the two subsets best agree with the similarity proportions of those subsets.

In an example, the first comparison comprises the first ratio being subtracted from an average value of the at least one outcome probability for the at least one medical condition for each patient record of the first sub-set of patient records. The second comparison comprises the second ratio being subtracted from an average value of the at least one outcome probability for the at least one medical condition for each patient record of the second sub-set of patient records.

In an example, determination of the second set of patient records comprises utilization of a magnitude of the at least one comparison.

In this way a simple metric can be used to determine the second "target" set of patient records, which can relate to a comparison and even an equating of predicted and actual outcome probabilities of medical conditions.

In an example, the processing unit is configured to iteratively decrease the number of records in the second set of patient records comprising utilisation of the at least one attribute value for the patient records in the second set of patient records. The records in the reduced second set of patient records are chosen such that there is an associated reduction in the magnitude of the at least one comparison.

In an example, the iteration proceeds until the magnitude of the at least one comparison falls below a threshold value.

In an example, the reduction in the number of records in the second set of patient records comprises utilisation of the at least one attribute value relating to the at least one medical condition for the second set of patient records prior to the reduction.

In an example, the at least one outcome probability for the at least one medical condition for each patient record of the first set of patient records comprises a probability relating to the positive outcome or negative outcome for the at least one medical condition.

In an example, each patient record comprises information relating to an outcome of the at least one medical condition. Separation of the first set of patient records into patient records relating to a positive outcome for the at least one medical condition and into patient records relating to a negative outcome for the at least one medical condition comprises utilization of the information relating to an outcome of the at least one medical condition.

In an example, the at least one medical condition comprises a medical outcome and wherein the user is presented with a list of medical outcomes from which the at least one query is selected.

In an example, the processing unit is configured to select the model from a plurality of available models based on the at least one query input by the user.

In this way, the most appropriate model to be implemented can be chosen that best generalizes the cases available from the patient database (e.g. best predictive power measured by precision and recall, which are evaluated on a random hold-out subset from the patient database not used in constructing the model).

According to a second aspect, there is provided a system for patient record identification, comprising:
a patient database;
an apparatus for patient record identification according to the first aspect; and
an output unit.

The patient records are provided from the patient database to the input unit, and the output unit is configured to output the second set of patient records.

In an example, the output unit is configured to output a first dataset comprising the first sub-set of patient records of the second set of patient records and the associated at least one outcome probability for the at least one medical condition for each patient record. The output unit is configured also to output a second dataset comprising the second sub-set of patient records of the second set of patient records and the associated at least one outcome probability for the at least one medical condition for each patient record.

According to a third aspect, there is provided a method for patient record identification, comprising:
a) inputting at least one query value relating to at least one medical condition;
b) receiving patient records from a patient database, wherein each patient record comprises at least one attribute value relating to the at least one medical condition, and wherein each patient record comprises information relating to an outcome of the at least one medical condition;
c) determining a first set of patient records based on a similarity between the at least one query value input by the user and the at least one attribute value for the patient records;
d) separating the first set of patient records into patient records relating to a positive outcome for the at least one medical condition and into patient records relating to a negative outcome for the at least one medical condition;
e) calculating by an implemented model at least one outcome probability for the at least one medical condition for each patient record of the first set of patient records based on the at least one attribute value for each patient record of the first set of patient records; and
f) determining a second set of patient records from the first set of patient records comprising at least one comparison comprising utilization of a number of patient records in a first sub-set of the patient records relating to the positive outcome and a number of patient records in a second subset of the patient records relating to the negative outcome and the at least one outcome probability for the at least one medical condition for each patient record of the first sub-set and second sub-set of the patient records.

According to another aspect, there is provided a computer program element controlling apparatus and/or system as previously described which, if the computer program element is executed by a processing unit, is adapted to perform the method steps as previously described.

There is also provided a computer readable medium having stored the computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
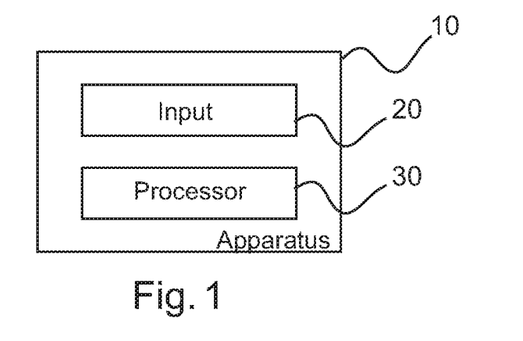
FIG. 1 shows a schematic set up of an example of an apparatus for patient record identification.

FIG. 1 shows an example of an apparatus 10 for patient record identification. The apparatus 10 comprises an input unit 20, and a processing unit 30. The input unit 20 is configured to enable a user to input at least one query value relating to at least one medical condition. The input unit 20 is configured also to receive patient records from a patient database. Each patient record comprises at least one attribute value relating to the at least one medical condition. The processing unit 30 is configured to determine a first set of patient records based on a similarity between the at least one query value input by the user and the at least one attribute value for the patient records. The processing unit 30 is configured also to separate the first set of patient records into patient records relating to a positive outcome for the at least one medical condition and separate the first set of patient records into patient records relating to a negative outcome for the at least one medical condition. The processing unit 30 is configured also to implement a model to calculate at least one outcome probability for the at least one medical condition for each patient record of the first set of patient records based on the at least one attribute value for each patient record of the first set of patient records. The processing unit 30 is configured also to determine a second set of patient records from the first set of patient records. The determination comprises at least one comparison comprising utilization of a number of patient records in a first sub-set of the patient records relating to the positive outcome. The at least one comparison also comprises utilization of a number of patient records in a second subset of the patient records relating to the negative outcome. The at least one comparison also comprises utilization of the at least one outcome probability for the at least one medical condition for each patient record of the first sub-set and second sub-set of the patient records.

In an example, the at least one medical condition comprises cardiovascular disease (CVD). In an example, the medical outcome can be or relate to cardiovascular death and major adverse cardiovascular events (MACE).

In an example, the at least one attribute value comprises one or more of: demographic information, life style information, medical information, care provider information, history and risk factor information, previous visit information, procedure information, etc. of a specific patient. The medical information includes a patient's basic health information, lesion information, device information and follow-up information. The at least one attribute can therefore can include demographic data (age, gender, weight, ethnicity, et cetera); presence/absence of chronic behavioural conditions (smoking, heavy alcohol consumption, consumption of various recreational drugs, et cetera); presence/absence of various chronic clinical conditions (high blood pressure, diabetes, asthma, heart disease; et cetera); presence/absence of various acute ailments (pneumonia or other acute respiratory ailments, various oncological conditions, or so forth); features related to same (e.g., cancer stage and grade); medical and care provider information and so forth. Thus, the at least one attribute value are data fields in a medical record, which can represent medical issues, for example, a symptom (e.g. bleeding), a severe medical result (e.g. death) or a medical status (e.g. normal), or other contextual information, for example, medical histories, lab test results or demographic data of a patient. The attribute value may be the value of contextual information or the likelihood of a medical issue for example.

According to an example, the at least one comparison comprises a first comparison between a first ratio of the number of patient records in the first sub-set of the patient records to the number of patient records in the second set of patient records with an average value of the at least one outcome probability for the at least one medical condition for each patient record of the first sub-set of patient records. The at least one comparison also comprises a second comparison between a second ratio of the number of patient records in the second sub-set of the patient records to the number of patient records in the second set of patient records with an average value of the at least one outcome probability for the at least one medical condition for the patient records of the second sub-set of patient records.

According to an example, the first comparison comprises the first ratio being subtracted from an average value of the at least one outcome probability for the at least one medical condition for each patient record of the first sub-set of patient records. In this example, the second comparison comprises the second ratio being subtracted from an average value of the at least one outcome probability for the at least one medical condition for each patient record of the second sub-set of patient records.

According to an example, determination of the second set of patient records comprises utilization of a magnitude of the at least one comparison.

According to an example, the processing unit is configured to iteratively decrease the number of records in the second set of patient records comprising utilisation of the at least one attribute value for the patient records in the second set of patient records. The records in the reduced second set of patient records are chosen such that there is an associated reduction in the magnitude of the at least one comparison.

According to an example, the iteration proceeds until the magnitude of the at least one comparison falls below a threshold value.

According to an example, the reduction in the number of records in the second set of patient records comprises utilisation of the at least one attribute value relating to the at least one medical condition for the second set of patient records prior to the reduction.

According to an example, the at least one outcome probability for the at least one medical condition for each patient record of the first set of patient records comprises a probability relating to the positive outcome or negative outcome for the at least one medical condition.

In an example, the at least one query comprises the at least one medical condition.

According to an example, each patient record comprises information relating to an outcome of the at least one medical condition. Separation of the first set of patient records into patient records relating to a positive outcome for the at least one medical condition and into patient records relating to a negative outcome for the at least one medical condition then comprises utilization of the information relating to an outcome of the at least one medical condition.

According to an example, the at least one medical condition comprises a medical outcome and wherein the user is presented with a list of medical outcomes from which the at least one query is selected.

According to an example, the processing unit is configured to select the model from a plurality of available models based on the at least one query input by the user.

Figure 2:
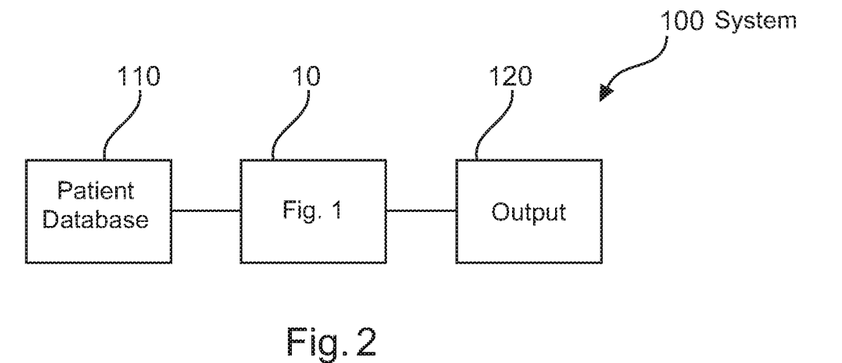
FIG. 2 shows a schematic set up of an example of a system for patient record identification.

FIG. 2 shows an example of a system 100 for patient record identification. The system 100 comprises a patient database 110, an apparatus 10 for patient record identification as described in any of the examples or combinations of examples described with respect to FIG. 1, and an output unit 120. The patient records are provided from the patient database to the input unit 20, and the output unit 120 is configured to output the second set of patient records.

According to an example, the output unit is configured to output a first dataset comprising the first sub-set of patient records of the second set of patient records and the associated at least one outcome probability for the at least one medical condition for each patient record. The output unit is configured also to output a second dataset comprising the second sub-set of patient records of the second set of patient records and the associated at least one outcome probability for the at least one medical condition for each patient record.

Figure 3:
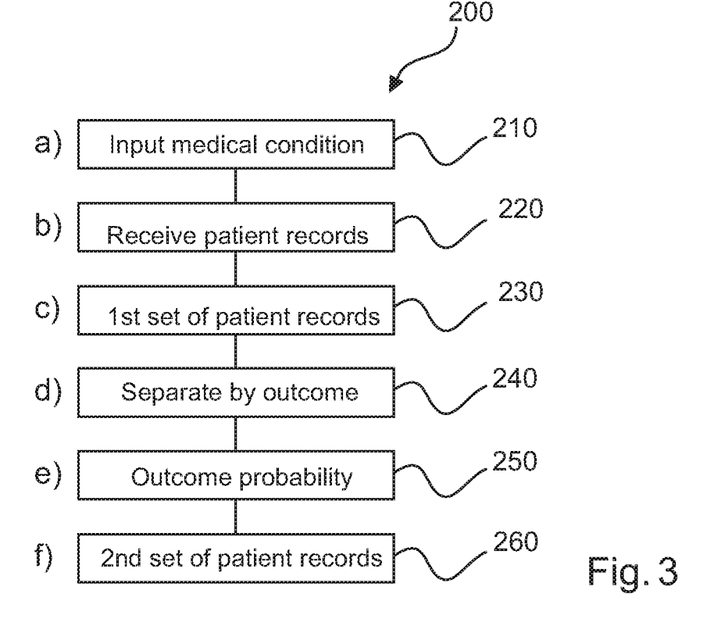
FIG. 3 shows a method for patient record identification.

FIG. 3 shows a method 200 for patient record identification in its basic steps. The method 200 comprises:

in an inputting step 210, also referred to as step a), inputting at least one query value relating to at least one medical condition;

in a receiving step 220, also referred to as step b), receiving patient records from a patient database, wherein each patient record comprises at least one attribute value relating to the at least one medical condition, and wherein each patient record comprises information relating to an outcome of the at least one medical condition;

in a determining step 230, also referred to as step c), determining a first set of patient records based on a similarity between the at least one query value input by the user and the at least one attribute value for the patient records;

in a separating step 240, also referred to as step d), separating the first set of patient records into patient records relating to a positive outcome for the at least one medical condition and into patient records relating to a negative outcome for the at least one medical condition;

in a calculating step 250, also referred to as step e), calculating by an implemented model at least one outcome probability for the at least one medical condition for each patient record of the first set of patient records based on the at least one attribute value for each patient record of the first set of patient records; and in a determining step 260, also referred to as step f), determining a second set of patient records from the first set of patient records comprising at least one comparison comprising utilization of a number of patient records in a first sub-set of the patient records relating to the positive outcome and a number of patient records in a second subset of the patient records relating to the negative outcome and the at least one outcome probability for the at least one medical condition for each patient record of the first sub-set and second sub-set of the patient records.

In an example, step f) comprises a first comparison between a first ratio of the number of patient records in the first sub-set of the patient records to the number of patient records in the second set of patient records with an average value of the at least one outcome probability for the at least one medical condition for each patient record of the first sub-set of patient records and comprises a second comparison between a second ratio of the number of patient records in the second sub-set of the patient records to the number of patient records in the second set of patient records with an average value of the at least one outcome probability for the at least one medical condition for the patient records of the second sub-set of patient records.

In an example, the first comparison comprises the first ratio being subtracted from an average value of the at least one outcome probability for the at least one medical condition for each patient record of the first sub-set of patient records; and wherein the second comparison comprises the second ratio being subtracted from an average value of the at least one outcome probability for the at least one medical condition for each patient record of the second sub-set of patient records.

In an example, step f) comprises utilizing a magnitude of the at least one comparison.

In an example, wherein the processing unit is configured to iterate step f) to iteratively decrease the number of records in the second set of patient records comprising utilising the at least one attribute value for the patient records in the second set of patient records, wherein the records in the reduced second set of patient records are chosen such that there is an associated reduction in the magnitude of the at least one comparison.

In an example, the iteration proceeds until the magnitude of the at least one comparison falls below a threshold value.

In an example, the reduction in the number of records in the first set of patient records comprises utilising the at least one attribute value relating to the at least one medical condition for the first set of patient records prior to the reduction.

In an example, in step e) the at least one outcome probability for the at least one medical condition for each patient record of the first set of patient records comprises a probability relating to the positive outcome or negative outcome for the at least one medical condition.

In an example, in step a) the at least one query comprises the at least one medical condition.

In an example, each patient record comprises information relating to an outcome of the at least one medical condition, and wherein step d) comprises utilizing the information relating to an outcome of the at least one medical condition.

In an example, the at least one medical condition comprises a medical outcome and wherein in step a) the user is presented with a list of medical outcomes from which the at least one query is selected.

In an example, step e) comprises selecting the model to implement from a plurality of available models based on the at least one query input by the user.

Figure 4:
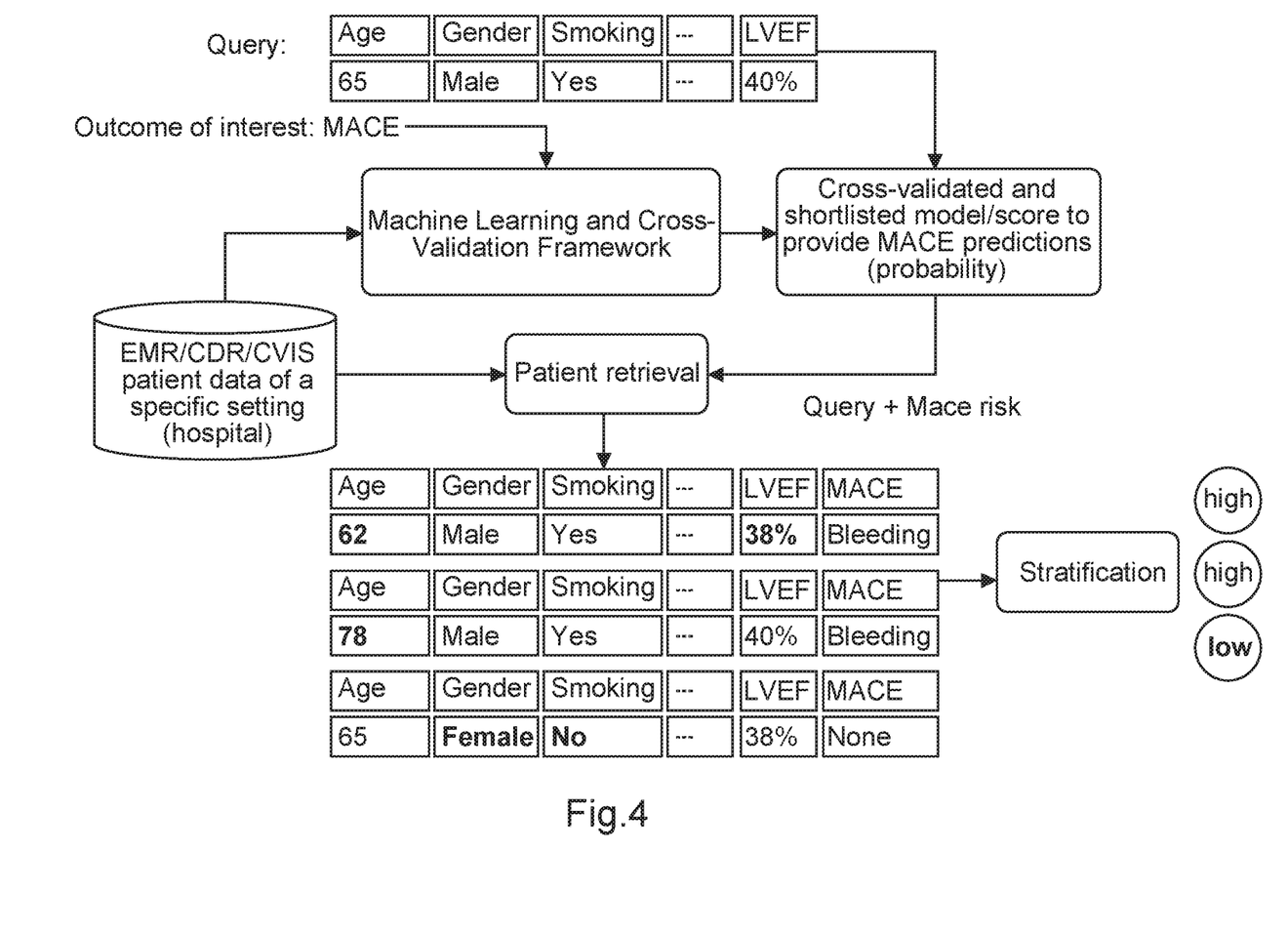
FIG. 4 shows a detailed high-level view of a system for patient record identification.

The apparatus, system and method for patient record identification are now described in more detail in conjunction with FIG. 4.

FIG. 4 shows a high level view of a whole patient record identification, retrieval and stratification system. As discussed above, Cardiovascular Information Systems (CVIS) have been available for many years in the healthcare industry. The main function of current CVIS is to store and assess patients' record—see for example U.S. Pat. No. 6,604,115B1. Some sophisticated CVIS are also integrated with other systems in the hospital such as Electronic Health Record (EHR), Laboratory Information System (LIS), etc. As such, a physician will have an overview of patients' health record. Usually a CVIS is used for reporting, scheduling and management purposes, whilst a Clinical Data Repository (CDR) further records more in-depth attributes (properties) for a specialized area such as cardiology. CDR provides richer and much more detailed information for performing advanced data analytics such as modeling and predictive analytics. The apparatus, method and system for patient record identification as described with respect to FIGS. 1-3, embodied in the exemplar system shown in FIG. 4 provides a directly integrated module in the CVIS/CDR to allow users/physicians to turn the information stored into knowledge effective and efficiently. It enables historical cases to be found that match certain new patient or query criteria, with for example only information of demographics and lab tests prior to a procedure. It helps the care providers to make decisions to retrieve from CDR matched patients whose post-procedure and follow-up events are available. The system and associated method retrieves case matches of a query patient with certain observed properties. The retrieval is done according to not only the observed properties but also its CVD probability of specified outcomes such as cardiovascular death and MACE. The probability (or risk) is embedded as a higher weighted property over properties observed in the query in the matching and retrieval process. The probability embedded is shortlisted from a series of models and CVD risk scores (e.g. GRACE, Framingham) after cross-validation on past cases with such labels. The models to generate such probabilities from the labelled cases are learned in a data-driven way handling imbalance challenges in CVD events. With the matched cases retrieved, they can be stratified according to categorization on the CVD outcome probability and user decisions. Similarly, a set of queries other than a single one can also be stratified in the same way and care providers can act accordingly to the stratification. Using a machine learning framework with cross-validation is able to shortlist a model from a series of machine learning methods (e.g. decision trees, support vector machine) that best generalizes the past cases on a specified outcome target, no matter the corresponding risk scores exist or not. As a result, the set of patients retrieved, considering this probability, results in more relevant past cases being identified for retrieval with the outcome of interest. However, different from pure patient matching and retrieval with observed properties, combining the outcome probability learned from CDR/CVIS is not adding yet another property. On one hand, the model that best generalizes the specified outcome probability may use only a small sub-set of properties (called features). The CVD outcome features may not overlap well with the observed query properties. Therefore, in the retrieval considering both observed properties and the to-be-calculated underlying outcome probability, non-trivial handling is desired to balance the matching on both sides properly.

Continuing with FIG. 4, the user inputs a set of query criteria, or a query patient without all of the properties available (e.g. CVD outcome), which is denoted as $Q=\{q_1, q_2, \ldots, q_p\}$.

For a specified CVD outcome of interest, e.g. MACE, a CDR (EMR/CVIS) based machine learning and cross-validation framework is (pre-) executed where a series of machine learning models $M=\{M_1, M_2, \ldots, M_k\}$ are trained and cross-validated on past case data, and the top model MT that best generalizes the data is selected to provide calculation of outcome probability.

A similarity metric is applied on the query Q and a set of loosely matched past cases (candidate set S) can be retrieved. On this candidate set there are labels of the actual outcome, separating S into S+ (outcome positive) and S− (outcome negative). The matching mechanism, considering both similarity and outcome probability, shortlists subsets S'+ and S'− from S+ and S−, so that the outcome probabilities of S'+ and S'− best agree with the similarity proportions.

In an example, this is done via minimizing an inconsistent score of outcome probabilities and similarities. In particular, an example shown below iteratively sets more stringent similarity thresholds to minimize the absolute difference (abs) between average (avg) outcome probabilities of S'+ and S'+ proportions, as well as that of S'−.

Pseudocode of an Example Embodiment

Input: $Q = \{q_1, q_2, \ldots, q_p\}$, selected outcome, and similarity metric, CDR data D (with p attributes and outcomes available), top model $M_T$ selected after cross-validation on D
Calculate all distances $dis_i$ between Q and data $D_i \in D$, so that a candidate set $S \subseteq D$ is retrieved, with the maximal distance = t (optionally truncated by preset similarity threshold t)
According to outcome labels, separate S into S+ and S−
S'+←S+, S'−←S−, S'←S'+ ∪ S'−
Sort all unique distances in descending order into $\{dis_1, dis_2, \ldots, dis_x\}$
Apply model $M_T$ on S'+ to calculate outcome probabilities prob(S'+)
Apply model $M_T$ on S'− to calculate outcome probabilities prob(S'−)
Inconsistent score sc ← abs(avg(prob(S'+)) − #(S'+)/#(S')) + abs(avg(prob(S'−)) − #(S'−)/#(S'))
For i = 1 to x-1
{
   S'+ ← S'+ − {d| d ∈ S'+, $dis_d <= dis_i$}
   S'− ← S'− − {d| d ∈ S'−, $dis_d > dis_i$}
   S' ← S'+ ∪ S'−
   Update inconsistent score sc'
   if(sc' < sc) sc ← sc'
}
Output all S'+ and S'− and the outcome probabilities In other examples, individual probability difference other than average, and other combinations than summation such as harmonic mean, can be adapted for the inconsistent score by someone with ordinary skills in this area. On the other hand, one can also implement maximization of a consistent score with the same purpose.

After S'+ and S'− are retrieved, they can be stratified through categorization on the CVD outcome probabilities, on the actual outcomes, and further on the grouping of the matched properties. In one example, users are provided an interactive interface to select the properties (probability, actual outcome, or matched properties) to organize the categorization as well as stratification weights. Besides a single query, the user can fetch multiple queries (patients without the actual outcome label) when retrieving past case patients queries (patients with the actual outcome label). The multiple query patients can also be stratified using the same stratification mechanism.

Summary of the Apparatus, System and Method for Patient Record Identification:

1. A patient retrieval system to consider matching both query properties and CVD outcome risk from historical cases in CDR.

The system provides a list of (predefined or configurable) CVD outcomes that can be selected by the user, and an interface for the user to input query properties or search a current patient whose CVD outcome may be unknown;

Given a set of observed properties (in the query), the system is able to transform them into two forms: one for approximate matching of properties of past patient cases in the CDR, and the other for calculating a model probability—as detailed in 2 (below);

The system, based on the matching mechanism—as detailed in 3 (below), is able to retrieve (get) and display a set of historical patients whose specified outcomes are known.

2. A machine learning and cross-validation framework to choose risk models for specified CVD outcome.

The framework uses multiple machine learning methods and cross-validation to learn (construct) models that generalize from the historical cases in the CDR;

The framework optionally accepts existing risk scores of a specified target as the model candidates, and applies the cross-validation to find thresholds of the scores that best generalize from the historical cases in the CDR;

The framework chooses from multiple learned models (as well as risk scores with thresholds if available) according to cross-validation performance on predicting the outcome;

The framework optionally has specialized mechanisms of up-/down-sampling and/or boosting to handle imbalance of the specified CVD outcome target.

Thus, taking a set of historical data (patient records) which has at least one attribute and another attribute of the specified CVD outcome, and in each row (each patient record) all these attributes' values including the outcome are known. From this set of historical data a prediction model can be trained (learned from the labelled data), and certain predictive performance measure can be calculated using certain evaluation methods on this data. One such evaluation method is here called "cross-validation". Therefore, for a certain specified outcome (e.g. MACE=Yes), only a small proportion of the historical data would have value "Yes" while the majority remaining would have "No". This is a challenge for predictive model training, and therefore the system re-samples the minority "Yes" data to make the "Yes"/"No" ratio more balanced. From multiple choices of established prediction modeling methods, the modeling method is chosen that has the best predictive performance measure in the evaluation. For any new case that has all or part of the attributes of the historical data, but not the specified outcome's value, the chosen best model then gives a probability of the outcome being "Yes".

3. A matching and stratification component that combines query property matching and CVD outcome risk in a balanced manner.

The matching component has to allow approximate matching (i.e. matching one or more attributes of historical patient data and the new query) according to the chosen similarity metric (see below for similarity metric details);

The component filters a loosely retrieved set of cases, which contains both positive and negative CVD outcomes as well as their modelled CVD outcome probabilities (as mentioned in 2 above), to maximize the consistency between the projected outcome probability and the positive/negative probability via controlling the similarity stringency;

The component is able to project the properties (for the attributes available in the historical patient data but not available in the query, the method can still compute similarity metric based only on the available attributes in the query) that are not available in the query but required for calculating the CVD outcome probability from the filtered set;

With the stratification part, retrieved cases can be stratified through categorization on the CVD outcome risk (e.g. setting thresholds on the probability), on the actual outcomes, and further on the grouping of the matched properties;

For a plurality of queries (patients without the actual outcome label), they can also be stratified using the same stratification mechanism.

Similarity Metric

A similarity metric here refers to the measurement of similarity between two vectors of values with equal lengths. The vector can be mixture of numeric and categorical values, but elements in the same positions of the two vectors must be in the same type.

For categorical values, the similarity metric can be distances such as Hamming distance (the number of different values in total in the two vectors).

For numeric values, the similarity metric can be distances such as Euclidean distance (L-2 distance) or L-1 distance which is defined as:

$$d_1(p, q) = \|p - q\| = \sum_{i=1}^{n} |p_i - q_i|$$

Where (p, q) are vectors.

$P=(p_1, p_2, \ldots p_n)$ and $q=(q_1, q_2, \ldots q_n)$.

For example, in the plane, the L-1 distance between $(p_1, p_2)$ and $(q_1, q_2)$ is: $|p_1-q_1|+|p_2-q_2|$.

For mixed vectors, one can either convert all categorical values into numeric values so that they can be handled the same way as numeric values, or convert numeric distances beyond a certain threshold as different so that they can be handled the same way as categorical values.

Inconsistent Score

The inconsistent score is, in an example, the difference between the positive (MACE="Yes") and the negative (MACE="No") subsets of historical data (patients) outcomes. The inconsistent score can be measured by the overall differences of outcome probabilities and the overall similarities between the two subsets.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for patient record identification, comprising:
   a user interface configured to receive a plurality of medical condition query values input by a user;
   a processor configured to:
      receive patient records from a patient database, wherein each patient record comprises a plurality of medical condition attribute values;
      determine a first set of patient records based on a similarity between the medical condition query values input by the user and the medical condition attribute values received from the patient database;
      separate the first set of patient records into a first sub-set of patient records in which a positive outcome was achieved for the medical condition and a second sub-set of patient records in which a negative outcome was achieved;
      for a user specified target outcome, execute machine learning and cross validation including training and cross validating a series of machine learning methods on prior patient records;
      select a model from the series of machine learning methods which best generalizes the patient records;
      using the selected model, calculate outcome probabilities for the positive outcome and the negative outcome for each patient record of the first set of patient records using the medical condition attribute values for each patient record of the first set of patient records;
      compute a first ratio of a number of patient records in the first sub-set of the patient records to a number of patient records in the first set of patient records;
      compute a second ratio of a number of patient records in the second sub-set of the patient records to the number of patient records in the first set of patient records for each patient record of the second sub-set of patient records;
      subtract the first ratio from the average value of the outcome probability for the medical condition for each patient record of the first sub-set of patient records;
      subtract the second ratio from an average value of the outcome probability for the medical condition for each patient record of the second sub-set of patient records; and
      iteratively decrease the number of records in the second sub-set of patient records until a magnitude of a difference between the first and second sub-sets of patient records falls below a threshold value; and
   a display configured to display a user-selected at least one of the first sub-set of patient records and the associated at least one outcome probability for each patient record, and the reduced second sub-set of patient records and the associated at least one outcome probability for each patient record.

2. The apparatus according to claim 1, wherein the outcome probability for the medical condition for each patient record of the first set of patient records comprises a probability of one of the positive outcome or the negative outcome for the medical condition.

3. The according to claim 1, wherein the user is presented with a display of a list of medical outcomes from which the at least one query is selected.

4. A method for patient record identification, comprising:
   a) inputting cardiovascular query values of a candidate patient;
   b) receiving patient records from a patient database, wherein each patient record comprises at least one cardiovascular physiological attribute value and wherein each patient record comprises one of a positive outcome including a major adverse cardiovascular event (MACE) or death or a negative outcome including a lack of a MACE or death;
   c) determining a first set of patient records having similar attribute values to the cardiovascular query values;
   d) separating the first set of patient records into a first sub-set of patient records in which the positive outcome was achieved and a second sub-set of patient records in which the negative outcome was achieved;
   e) iteratively reducing a number of patient records in the second sub-set until a difference between a number of records in the first and second sub-sets falls below a preselected threshold;

f) executing machine learning and cross-validation including training and cross-validating a series of machine learning methods on the patient records;

g) selecting a model from the series of machine learning methods which best generalize patient records for a user specified positive outcome;

h) calculating with the selected model at least one outcome probability for each patient record of the first set of patient records based on the cardiovascular attribute values for each patient record of the first set of patient records; and i) controlling a display device to display a user selected one of the patient records of the first sub-set of patient records in descending order of outcome probability and the patient records of the second sub-set of patient records in descending order of outcome probability.

5. A non-transitory computer-readable medium carrying a computer program configured to control a processor to carry out the method of claim 4.

6. The apparatus according to claim 1, in which the attribute and query values include one or more of demographic information, lifestyle information, medical information, care provider information, history and risk factor information, previous visit information, and procedure information of a specific patient.

7. The method according to claim 4, in which the cardiovascular attribute and query values include one or more of demographic information, lifestyle information, medical information, care provider information, history and risk factor information, previous visit information, and procedure information of a specific patient.

8. The apparatus according to claim 1, wherein the query and attribute values include patient health information, lesion information, follow-up information, demographic data, presence/absence of chronic behavioral conditions including smoking, heavy alcohol consumption, consumption of various recreational drugs, presence/absence of various chronic clinical conditions including high blood pressure, diabetes, asthma, and heart disease, presence/absence of various acute ailments including pneumonia and other respiratory ailments, and oncology conditions, symptoms, medical results including death, normal and context information including medical histories, lab test results, and demographic data.

9. The method according to claim 4, wherein the cardiovascular query and attribute values include patient health information, lesion information, follow-up information, demographic data, presence/absence of chronic behavioral conditions including smoking, heavy alcohol consumption, consumption of various recreational drugs, presence/absence of various chronic clinical conditions including high blood pressure, diabetes, asthma, and heart disease, presence/absence of acute ailments including pneumonia and other respiratory ailments, and various oncology conditions, symptoms, medical results including death, normal and context information including medical histories, lab test results, and demographic data.

* * * * *